(12) United States Patent
Pfeuffer

(10) Patent No.: US 8,203,340 B2
(45) Date of Patent: Jun. 19, 2012

(54) MAGNETIC RESONANCE METHOD AND APPARATUS FOR GENERATING A PERFUSION IMAGE

(75) Inventor: Josef Pfeuffer, Newton, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 982 days.

(21) Appl. No.: 12/189,241

(22) Filed: Aug. 11, 2008

(65) Prior Publication Data

US 2010/0036234 A1 Feb. 11, 2010

(51) Int. Cl.
*G01V 3/00* (2006.01)
(52) U.S. Cl. ........................................ 324/309; 324/307
(58) Field of Classification Search .......... 324/300–322; 600/407–445
See application file for complete search history.

(56) References Cited

U.S. PATENT DOCUMENTS

| | | | |
|---|---|---|---|
| 5,402,785 A | 4/1995 | Leight et al. | |
| 6,271,665 B1* | 8/2001 | Berr et al. | 324/306 |
| 7,047,060 B1* | 5/2006 | Wu | 600/410 |
| 2010/0016706 A1* | 1/2010 | Wohlgemuth | 600/410 |
| 2010/0141254 A1* | 6/2010 | Pfeuffer | 324/309 |
| 2010/0240983 A1* | 9/2010 | Jung et al. | 600/410 |
| 2011/0184288 A1* | 7/2011 | Kawabata et al. | 600/440 |

* cited by examiner

*Primary Examiner* — Brij Shrivastav
(74) *Attorney, Agent, or Firm* — Schiff Hardin LLP

(57) ABSTRACT

In a magnetic resonance method and apparatus for generating perfusion images, a perfusion series of magnetic resonance perfusion images is acquired that includes tag images and at least one control image, that are grouped in pairs. From each pair an initially processed perfusion image is obtained, such as by subtraction. Each initially processed image is subjected to a quality control review by analysis with respect to at least one image quality criterion. Any initially processed image that does not satisfy the quality criterion is rejected. Only initially processed images that satisfy the quality criterion are combined to form a resultant magnetic resonance perfusion image. Artifacts in the resultant perfusion image are thereby reduced or avoided.

30 Claims, 2 Drawing Sheets

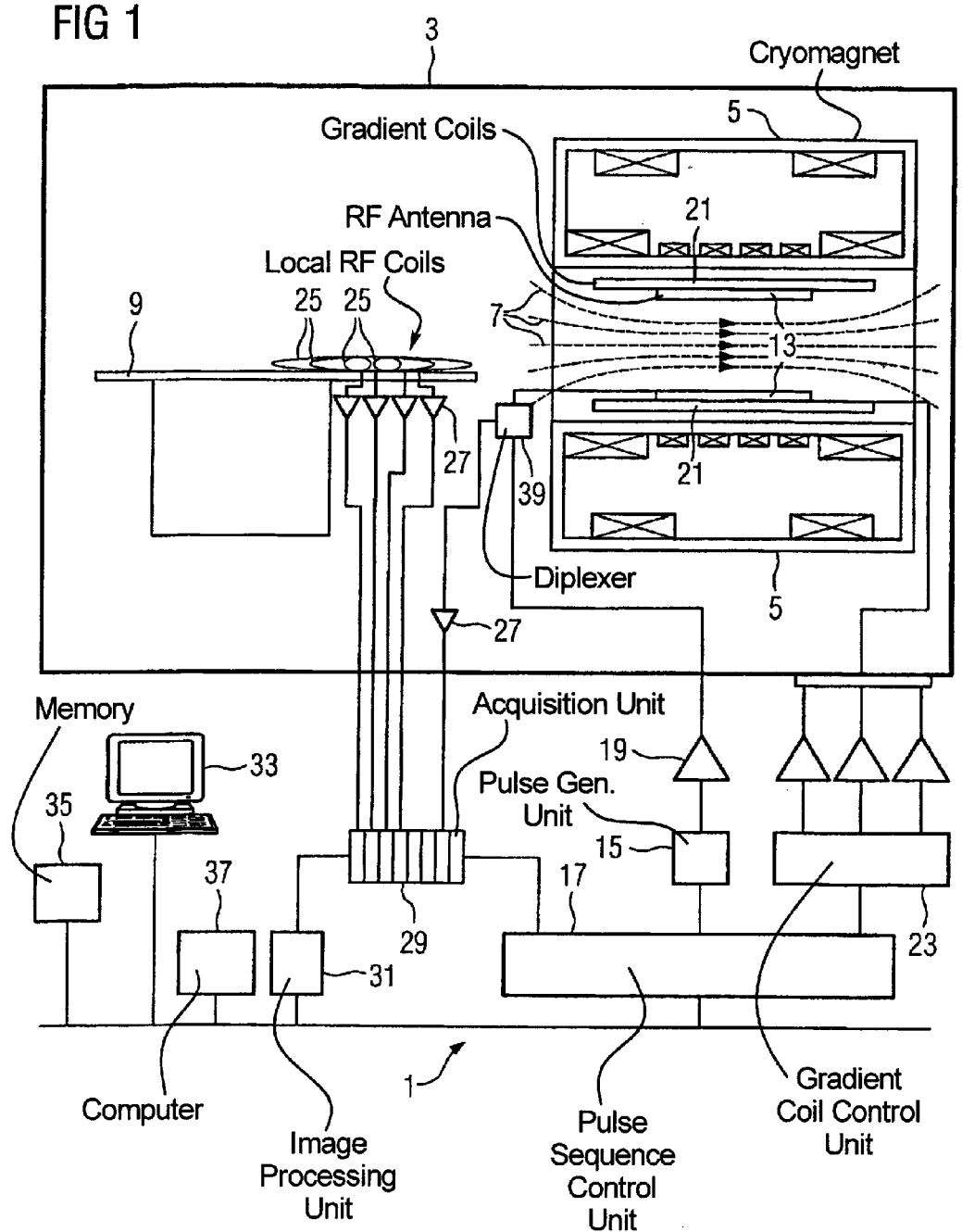

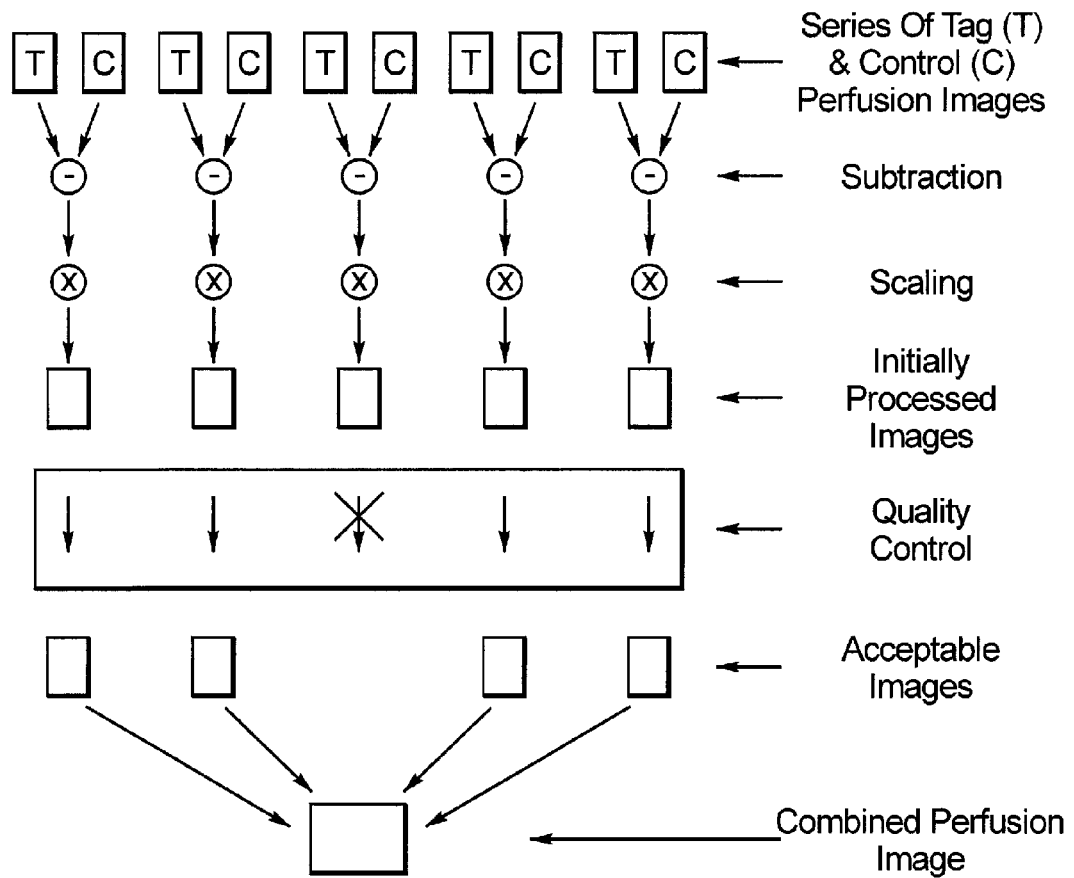
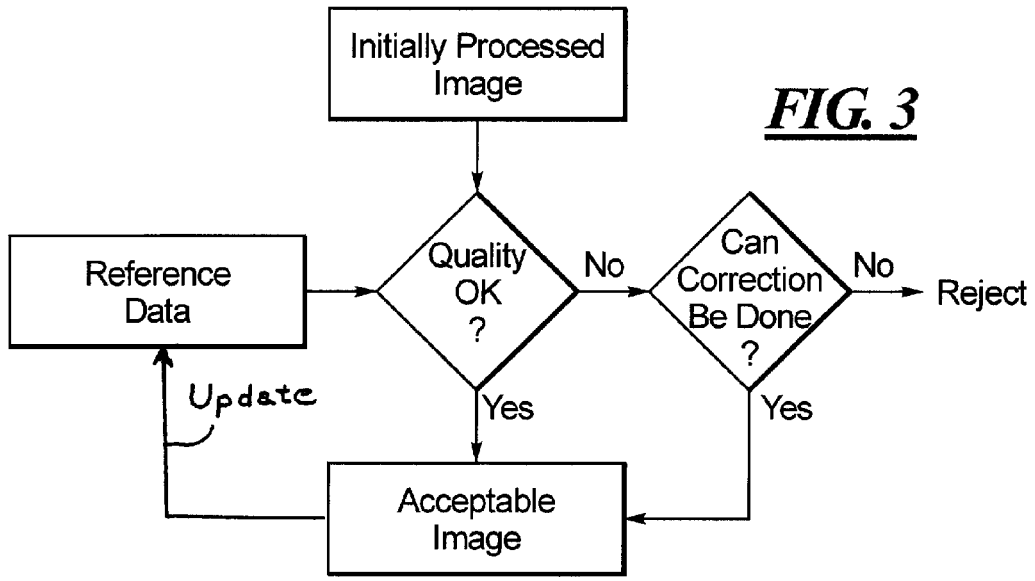

MAGNETIC RESONANCE METHOD AND APPARATUS FOR GENERATING A PERFUSION IMAGE

BACKGROUND OF THE INVENTION

1. Field of the Invention

The present invention relates to a method and an apparatus for generating magnetic resonance images, and in particular to a method and an apparatus for generating magnetic resonance perfusion images.

2. Description of the Prior Art

Magnetic resonance technology has been increasingly used in recent years to generate angiographic images since, relative to other medical imaging modalities such as, for example, radioscopy with x-rays or computed tomography, it has among other things, the advantage that patient and medical personal are subjected to no radiation exposure.

Magnetic resonance (MR) technology is a known technology with which images of the inside of an examination subject can be generated. For this purpose, the examination subject is positioned in a strong, static, homogeneous basic magnetic field (field strengths of 0.2 Tesla to 7 Tesla and higher) in an MR apparatus so that the subject's nuclear spins become oriented along the basic magnetic field. Radio-frequency excitation pulses are radiated into the examination subject to excite nuclear magnetic resonances, the excited nuclear magnetic resonances being measured (detected and MR images being reconstructed based thereon. For spatial coding of the measurement data, rapidly switched magnetic gradient fields are superimposed on the basic magnetic field. The acquired measurement data are digitized and stored as complex numerical values in a k-space matrix. An associated MR image can be reconstructed from the k-space matrix populated with such values by means of a multi-dimensional Fourier transformation.

Magnetic resonance can be used to produce images representing tissue perfusion, which is the flow of fluid in tissue. Perfusion studies allow an assessment to be made of the functioning of organs in vivo. For this purpose, in some techniques a contrast agent, which generates a signal that is detectable by magnetic resonance imaging, is injected into a subject, and the magnetic resonance data are acquired at a time when the contrast agent has optimally flowed into the region or anatomy of interest. Since the contrast agent is injected into the vascular system of the subject, the appearance of the contrast agent in the magnetic resonance image is representative of blood flow in the region or anatomy of interest. Magnetic resonance perfusion techniques are particularly useful in the context of magnetic resonance images of the head, in particular the brain, wherein cerebral blood flow (CBF) is identified. In another magnetic resonance perfusion technique using known arterial spin labeling (ASL) methods (which do not require injection of a contrast agent), images are often acquired with a perfusion-sensitive preparation (tag images) in alternation with non-perfusion-sensitive images (control images). The perfusion information in the tag images represents only a small change in the image contrast due to the inflowing tagged, i.e. magnetic resonance-labeled, spins into the region of interest, in the magnetic resonance images that are acquired. Typically, the perfusion signal is on the order of only a few percent of the total magnetic resonance image intensity.

Therefore, the extraction and quantification of relative perfusion images and quantitative perfusion images is prone to artifacts. Due to the low magnitude of the perfusion signal, multiple image acquisitions in the time frame of minutes are necessary. This results in a time series of images being acquired, with tag and control images alternating with each other. These tag and control images are combined with each other in pairs, by subtraction, so that multiple subtraction images are then available, which can be combined to form a resultant perfusion image. By combining multiple perfusion images, the low magnitude perfusion signal is made more readily visible in the combined image.

Due to the length of time that is necessary to acquire such an image series the most series source of image artifacts is patient movement, either gross (muscular) movement or natural movement such as respiration and cardiac motion. The control image is intended to be a static, snapshot image that can be ideally subtracted from the tag image that contains a small signal modulation originating from the perfusion. As noted above, this signal difference between the tag image and the control image is on the order of only a few percent. Artifacts can easily occur due to instabilities in the signal contribution to the control image, thereby causing the control image to deviate from a truly static image. In addition to non-static signal contributions originating within the examination subject, instabilities in the scanner that is used to acquire the magnetic resonance data may also cause the control image not to be truly static. An error as small as on the order of one percent in the control image can result in an artifact of approximately 100% false changes being attributed to the perfusion image.

As noted above, the typical processing that is employed to minimize this problem is to generate multiple perfusion images that are each a difference of a tag image and a control image. The multiple perfusion images are then averaged. A scaling or calibration factor can be applied to obtain a perfusion-weighted or a quantitative perfusion image. More advanced techniques use temporal interpolation methods of the time series of perfusion images, in order to recover the temporal resolution in the difference images. A typical procedure is to correct the original image series for motion before undertaking the averaging. This is accomplished by registering the image volumes of repeated measurements to a reference volume. This can significantly reduce the subtraction artifacts as long as the subsequent volumes can be fully registered. If motion artifacts occur within the volume, however, such volume-based registration fails, and leaves to significant subtraction artifacts, resulting in false perfusion images.

SUMMARY OF THE INVENTION

It is an object of the present invention to provide a method and apparatus for acquiring magnetic resonance perfusion images wherein the effect of motion artifacts is reduced, thereby improving the accuracy and quality of the resulting perfusion images.

The above object is achieved in accordance with the present invention in a method and apparatus for magnetic resonance perfusion imaging wherein the initially processed perfusion images, that respectively result from a processed combination, such as subtraction, of a tag image and a control image, are subjected to a quality control analysis before the initially processed images are combined to form the resultant perfusion image. In the quality control analysis, any initially processed image that fails to satisfy predetermined quality control criteria is rejected, and is not used in the subsequent averaging, or combining procedure, that is used to generate the combined perfusion image. Initially processed images that exhibit excessive motion artifacts therefore do not make a contribution to the combined perfusion image, so that the overall quality of the combined perfusion image is significantly improved.

The quality control can take place fully automatically in computerized fashion, or can be conducted with user interaction, so that a user can make his or her own judgment as to the level of quality of the images that will enter into the combining procedure to produce the combined perfusion image. Even if the procedure is implemented automatically, a user or operator still can be informed by an alarm or some other type of indicator if an excessive number of initially processed perfusion images of unacceptable quality are habitually occurring, so that the user or operator can take corrective steps in the settings of the magnetic resonance data acquisition system that is being employed for generating the magnetic resonance data.

In order to permit the user or the operator to undertake such appropriate corrective steps, the quality control analysis can be implemented in real time as the initially processed perfusion images are being acquired (generated). Alternatively, it is possible to generate the entire set of initially processed perfusion images and to then conduct the quality control analysis offline. In this embodiment, however, the final, combined perfusion images are not immediately available while the patient is still in the magnetic resonance data acquisition chamber.

BRIEF DESCRIPTION OF THE DRAWINGS

FIG. 1 schematically illustrates the basic components of a magnetic resonance imaging system constructed and operating in accordance with the present invention.

FIG. 2 schematically illustrates the method for obtaining a combined perfusion image in accordance with the present invention, embodying a quality control review of the initially processed perfusion images.

FIG. 3 is a flowchart illustrating an embodiment for implementing the quality control review in the method and apparatus according to the present invention.

DESCRIPTION OF THE PREFERRED EMBODIMENTS

FIG. 1 schematically shows the design of a magnetic resonance apparatus 1 with its basic components. In order to examine a body by means of magnetic resonance imaging, various magnetic fields tuned to one another as precisely as possible in terms of their temporal and spatial characteristics are applied.

A strong magnet (typically a cryomagnet 5 with a tunnel-shaped opening) arranged in a radio-frequency shielded measurement chamber 3 generates a static, strong basic magnetic field 7 that typically amounts to 0.2 Tesla to 3 Tesla and more. A body or a body part (not shown here) to be examined is borne on a patient bed 9 and positioned in the homogeneous region of the basic magnetic field 7.

The excitation of the nuclear spins of the body ensues via magnetic radio-frequency excitation pulses that are radiated via a radio-frequency antenna (shown here as a body coil 13). The radio-frequency excitation pulses are generated by a pulse generation unit 15 that is controlled by a pulse sequence control unit 17. After an amplification by a radio-frequency amplifier 19 they are relayed to the radio-frequency antenna. The radio-frequency system shown here is merely schematically indicated. Typically more than one pulse generation unit 15, more than one radio-frequency amplifier 19 and multiple radio-frequency antennas are used in a magnetic resonance apparatus 1.

Furthermore, the magnetic resonance apparatus 1 has gradient coils 21 with which magnetic gradient fields for selective slice excitation and for spatial coding of the measurement signal are radiated in a measurement. The gradient coils 21 are controlled by a gradient coil control unit 23 that, like the pulse generation unit 15, is connected with the pulse sequence control unit 27.

The signals emitted by the excited nuclear spins are acquired by the body coil 13 and/or by local coils 25, amplified by associated radio-frequency preamplifiers 27 and processed further and digitized by an acquisition unit 29.

Given a coil (such as, for example, the body coil 13) that can be operated both in transmission mode and in acquisition mode, the correct signal relaying is regulated by an upstream transmission-reception diplexer 39.

An image processing unit 31 generates from the measurement data an image that is presented to a user via an operator console 33 or is stored in a memory unit 35. A central computer 37 controls the individual system components. The computer 37 is thereby fashioned such that the method according to the invention can be implemented by appropriate programming of the computer 37.

The basic steps of the method in accordance with the present invention, that are implemented by appropriate programming of the computer 37 of the apparatus 1 shown in FIG. 1, are illustrated in FIG. 2. In the exemplary embodiment shown in FIG. 2, for conducting a perfusion study with ASL, a series of alternating tag T and control C images are generated. Other ASL acquisition schemes are possible, and are also encompassed with the scope of the present method and apparatus. For example, multiple tag images T can be acquired with only a single control image, or respective control images can be "shared" by more than one tag image (T1-C1, C1-T2, T2-C2, C2-T3, etc.). The basic concept of the present method and apparatus is to implement a quality control for any type of initially processed perfusion images.

In the exemplary embodiment of FIG. 2, the tag images T and control images C, in pairs, are subtracted from each other. If necessary or desired, appropriate scaling and/or weighting can be implemented on the subtraction image. This results in a number of initially processed images. Other ways, besides simple subtraction, are also possible for producing the initially processed images and are encompassed within the scope of the present method and apparatus.

In accordance with the present invention, the initially processed images are subjected to an automatic or user-interactive quality control. In the example shown in FIG. 2, the center initially processed image is determined not to satisfy the applicable quality control standard, and therefore does not pass through the quality control. This results in four acceptable images being available, which are then combined to form the resultant perfusion image. The non-inclusion of the initially processed image that did not satisfy the quality control analysis results in the combined perfusion image having a high image quality, and not being afflicted with motion artifacts.

An exemplary embodiment based on the procedure illustrated in FIG. 2 is as follows. In a magnetic resonance image for a perfusion study using arterial spin labeling, multiple states of perfusion information-containing images (tag images) and control images are acquired in a 2D or 3D volume, and this procedure is repeated multiple times for averaging so as to increase the signal-to-noise and the contrast-to-noise ratios in the final perfusion image. The tag and control images are acquired interleaved using the arterial spin labeling method tag-control-tag-control-tag, etc. The pairs of tag and control images are subtracted from each other to obtain a subtraction image, which contains only perfusion information. This subtraction image may be afflicted with motion artifacts.

The initially processed images are then subjected to the quality control review described above, which results in a number of acceptable images passing through the quality control. Only the acceptable images are combined to form the resultant perfusion image.

An exemplary embodiment of the quality control is illustrated in the flowchart of FIG. 3. The quality control procedure uses a metric comparison of the initially processed image being analyzed, with reference data. The reference data may be a reference image or a priori determined statistical data. If the comparison (Quality OK?) indicates that the appropriate quality level exists in the initially processed image, it is passed on as an acceptable image.

The reference data may be dynamically constructed and updated during the ongoing acquisition process, as shown in FIG. 3.

The metric comparison between the reference data and the image being analyzed can be based on the mean and/or standard deviation of the intensity distribution, or may be based on an energy analysis such as the root mean square of the energy content of the initially processed image, or may be an edge detection technique employing a grad operator or a Laplace operator, or may be other mutual information contained in a stored image and the initially processed image.

The quality control procedure can be implemented in real time during the ongoing data acquisition of the image series, or can be done offline using the image series.

The quality control can be implemented fully automatically or with user interaction. If done with user interaction, the user can manually review each initially processed image in order to pass each image along for making a contribution to the combined perfusion image. Even if the quality control is undertaken in a computerized, automatic manner, without user interaction, it is still possible to notify the user if any, or if a predetermined number, of initially processed images fails to pass through the quality control. This may indicate to the user that adjustments in the image acquisition process need to be made.

In the quality control procedure, as also indicated in FIG. 3, an initially processed image which is determined not to satisfy the requisite level of image quality may be analyzed to determine whether a correction by image processing can be undertaken that will result in the image still being suitable for use as an acceptable image for inclusion in the combined perfusion image. If no correction can be done, the initially processed image in question is rejected. If correction can be done, the correction is made and an acceptable image results.

Although modifications and changes may be suggested by those skilled in the art, it is the intention of the inventor to embody within the patent warranted hereon all changes and modifications as reasonably and properly come within the scope of his contribution to the art.

I claim:

1. A method for generating a magnetic resonance perfusion image, comprising the steps of:
   from a perfusion series of magnetic resonance images comprising a plurality of tag images and at least one control image, pairing said tag images and said at least one control image to produce a plurality of pairs and generating, from each pair, an initially processed magnetic resonance perfusion image;
   subjecting each initially processed image to a quality control review by analyzing each initially processed image with respect to at least one image quality criterion, and rejecting any of said initially processed images that do not satisfy said quality criterion, thereby obtaining a plurality of acceptable magnetic resonance perfusion images; and
   automatically combining only said acceptable magnetic resonance perfusion images to obtain, as an output, a resultant magnetic resonance perfusion image.

2. A method as claimed in claim 1 wherein each of said initially processed images exhibits an intensity distribution, and employing a mean and standard deviation of said intensity distribution as said quality criterion.

3. A method as claimed in claim 1 wherein each of said initially processed images exhibits an energy content, and employing the root mean square of said energy content as said quality criterion.

4. A method as claimed in claim 1 wherein each of said initially processed images comprises edge features, and implementing an edge detection technique as said quality criterion.

5. A method as claimed in claim 4 comprising implementing said edge detection technique with a grad operator.

6. A method as claimed in claim 4 comprising implementing said edge detection technique with a Laplace operator.

7. A method as claimed in claim 1 comprising employing a reference image as said quality criterion, and comparing each initially processed image to said reference image.

8. A method as claimed in claim 1 comprising completely automatically implementing said quality control review.

9. A method as claimed in claim 1 comprising implementing said quality control review with user interaction.

10. A method as claimed in claim 1 comprising implementing said quality control review offline after acquisition of said series.

11. A method as claimed in claim 1 comprising implementing said quality control review in real time with acquisition of said series.

12. A method as claimed in claim 11 comprising displaying a representation of said quality criterion during acquisition of said series.

13. A method as claimed in claim 11 comprising generating a humanly perceptible indicator if a predetermined number of rejections occur in said quality control review.

14. A method as claimed in claim 1 comprising generating said initially processed magnetic resonance perfusion image from each pair by subtracting the control image from the tag image in each pair.

15. A method as claimed in claim 1 comprising dynamically updating said image quality criterion during acquisition of said series dependent on a content of said acceptable magnetic resonance profusion images.

16. A magnetic resonance apparatus for generating a magnetic resonance perfusion image, comprising:
   a magnetic resonance data acquisition device configured to interact with a subject to acquire a perfusion series of magnetic resonance images comprising a plurality of tag images and at least one control image;
   an image processor configured to pair said tag images and said at least one control image to produce a plurality of pairs and to generate, from each pair, an initially processed magnetic resonance perfusion image;
   a quality control module configured to subject each initially processed image to a quality control review by analyzing each initially processed image with respect to at least one image quality criterion, and rejecting any of said initially processed images that do not satisfy said quality criterion, thereby obtaining a plurality of acceptable magnetic resonance perfusion images; and an image computer configured to automatically combine only said acceptable magnetic resonance perfusion images to obtain, as an output, a resultant magnetic resonance perfusion image.

17. A magnetic resonance apparatus as claimed in claim 16 wherein each of said initially processed images exhibits an intensity distribution, and wherein said quality control module is configured is to employ a mean and standard deviation of said intensity distribution as said quality criterion.

18. A magnetic resonance apparatus as claimed in claim 16 wherein each of said initially processed images exhibits an energy content, and wherein said quality control module is configured is to employ the root mean square of said energy content as said quality criterion.

19. A magnetic resonance apparatus as claimed in claim 16 wherein each of said initially processed images comprises edge features, and wherein said quality control module is configured is to implement an edge detection technique as said quality criterion.

20. A magnetic resonance apparatus as claimed in claim 19 wherein said quality control module is configured is to implement said edge detection technique with a grad operator.

21. A magnetic resonance apparatus as claimed in claim 19 wherein said quality control module is configured is to implement said edge detection technique with a Laplace operator.

22. A magnetic resonance apparatus as claimed in claim 16 wherein said quality control module is configured is to employ a reference image as said quality criterion, and comparing each initially processed image to said reference image.

23. A magnetic resonance apparatus as claimed in claim 16 wherein said quality control module is configured to completely automatically implement said quality control review.

24. A magnetic resonance apparatus as claimed in claim 16 wherein said quality control module is configured to implement said quality control review with user interaction.

25. A magnetic resonance apparatus as claimed in claim 16 wherein said quality control module is configured is to implement said quality control review offline after acquisition of said series.

26. A magnetic resonance apparatus as claimed in claim 16 wherein said quality control module is configured is to implement said quality control review in real time with acquisition of said series.

27. A magnetic resonance apparatus as claimed in claim 26 wherein said quality control module is configured is to display a representation of said quality criterion during acquisition of said series.

28. A magnetic resonance apparatus as claimed in claim 26 wherein said quality control module is configured is to generate a humanly perceptible indicator if a predetermined number of rejections occurs in said quality control review.

29. A magnetic resonance apparatus as claimed in claim 16 wherein said processor is configured to generate said initially processed magnetic resonance profusion images by, in each pair, subtracting the control image from the tag image.

30. A magnetic resonance apparatus as claimed in claim 16 wherein said quality control module is configured to update said image quality criterion during acquisition of said series dependent on an image content of said acceptable magnetic resonance profusion images.

* * * * *